US008831306B2

(12) United States Patent
Manri et al.

(10) Patent No.: US 8,831,306 B2
(45) Date of Patent: Sep. 9, 2014

(54) FLOW TYPE PARTICLE IMAGE ANALYSIS METHOD AND DEVICE

(75) Inventors: Chihiro Manri, Kawagoe (JP); Norio Oowada, Naka (JP); Satoshi Mitsuyama, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 362 days.

(21) Appl. No.: 13/375,249

(22) PCT Filed: May 17, 2010

(86) PCT No.: PCT/JP2010/058261
§ 371 (c)(1),
(2), (4) Date: Nov. 30, 2011

(87) PCT Pub. No.: WO2010/140460
PCT Pub. Date: Dec. 9, 2010

(65) Prior Publication Data
US 2012/0076349 A1    Mar. 29, 2012

(30) Foreign Application Priority Data
Jun. 3, 2009  (JP) ................. 2009-134212

(51) Int. Cl.
G06K 9/00   (2006.01)
G06K 9/40   (2006.01)
G01N 15/14  (2006.01)

(52) U.S. Cl.
CPC .... *G01N 15/1459* (2013.01); *G01N 2015/1452* (2013.01)
USPC ............................ 382/128; 382/255; 382/134

(58) Field of Classification Search
None
See application file for complete search history.

(56) References Cited

U.S. PATENT DOCUMENTS

| 5,275,951 A | 1/1994 | Chow et al. |
| 5,448,349 A | 9/1995 | Kosaka |
| 5,880,835 A | 3/1999 | Yamazaki et al. |
| 6,317,511 B1 * | 11/2001 | Horiuchi ................. 382/133 |

(Continued)

FOREIGN PATENT DOCUMENTS

| CN | 1086313 A | 5/1994 |
| JP | 63-94156 A | 4/1988 |

(Continued)

OTHER PUBLICATIONS

Japanese Office Action received in Japanese Application No. 2011-518372 Chinese Office Action received in Chinese Application No. 201080024498.

*Primary Examiner* — Stephen R Koziol
*Assistant Examiner* — Sean Conner
(74) *Attorney, Agent, or Firm* — Mattingly & Malur, PC

(57) ABSTRACT

At each of mutually different multiple focal positions, focal adjustment parameter values are obtained from images of standard particles made of the same substance. Each focal adjustment parameter value is figured out as any one of the ratio between the density value around the center of the standard particle image and the density value around the outline, the difference therebetween, and the density value around the center. The in-focus position is adjusted on the basis of the relationship between the obtained focal adjustment parameter values and the focal positions. Moreover, on the basis of the relationship between the focal adjustment parameter values and the focal positions, the parameter values are converted into focal positions, and the focal positions and dispersion thereof are used to check the displacement of the in-focus position and the thickness of the sample liquid.

10 Claims, 11 Drawing Sheets (a)

x-coordinate (b)

x-coordinate (c)

x-coordinate

(56) References Cited

U.S. PATENT DOCUMENTS

| | | | |
|---|---|---|---|
| 6,409,141 B1* | 6/2002 | Yamazaki et al. | 249/117 |
| 2004/0189818 A1* | 9/2004 | Tsuruoka et al. | 348/221.1 |
| 2005/0089191 A1* | 4/2005 | Yamaguchi et al. | 382/100 |
| 2005/0127271 A1* | 6/2005 | Ortyn et al. | 250/201.4 |
| 2007/0159627 A1* | 7/2007 | Johnson | 356/335 |
| 2007/0273878 A1* | 11/2007 | Fujii et al. | 356/337 |
| 2009/0226031 A1* | 9/2009 | Izuka | 382/100 |
| 2013/0258075 A1* | 10/2013 | Muraki et al. | 348/61 |

FOREIGN PATENT DOCUMENTS

| | | | |
|---|---|---|---|
| JP | 5-296915 A | | 11/1993 |
| JP | 6-507496 A | | 8/1994 |
| JP | 9-311102 A | | 12/1997 |
| JP | 2939647 B2 | | 6/1998 |
| JP | 2002-062251 | * | 2/2002 |
| JP | 2002-62251 A | | 2/2002 |
| JP | 2007-304059 A | | 11/2007 |

* cited by examiner

FLOW TYPE PARTICLE IMAGE ANALYSIS METHOD AND DEVICE

TECHNICAL FIELD

The present invention relates to a flow type particle image analysis method and device for capturing an image of a particle in a flow cell and analyzing the static image of the particle.

BACKGROUND ART

In conventional particle image analyses, morphological tests on cells in blood and particles in urine are performed through a procedure in which a laboratory personnel prepares a sample on a microscope slide and directly observes it through a microscope. Such microscopic tests have problems that the personnel's ability affects the results, the tests are time consuming, and so on, and are therefore desired to be made more efficient.

In recent years, with the advancement in automation of testing, Patent Documents 1 and 2, for example, have disclosed flow type particle image analysis devices in which: a sample is caused to flow through a flow cell having a special shape; particles in the sample are caused to flow through a wide imaging region; magnified images of the particles in the sample are captured as static images while a flash lamp is turned on; and the particles are classified based on the static images. The flow type particle image analysis devices create a flat flow of a sample liquid by causing it to flow through the flow cell having a special shape while surrounding the sample liquid with the flow of a sheath liquid on an outer side thereof. There are, however, cases where the shape of the flow of the sample liquid becomes thicker than a preset value due to such a reason that a predetermined amount of sheath liquid is not flowing or the flow of the sheath liquid is uneven. As the flow of the sample liquid becomes thicker, the positions of the particles are displaced from the in-focus position, making it impossible to obtain proper images in some cases.

Static images of particles need to be captured always at the in-focus position in order for the flow type particle image analysis devices to maintain the accuracy of their particle classification. To always obtain in-focus images, the following processes need to be performed, for example.

(1) The in-focus position is accurately adjusted at the time of the startup of the device.

(2) The in-focus position and the thickness of the flow of the sample liquid are regularly checked after (1) as well.

Focal adjustment methods regarding (1) are described in Patent Documents 3 to 5, for example. Patent Document 3 discloses a method in which in the adjustment of the focal point, static images of standard particles made of the same substance and having the same size (hereinafter, standard particles) are obtained at mutually different multiple positions by moving the flow cell or the field lens; the average area value of the standard particles at each of the positions is calculated; and the position of the flow cell or the field lens is adjusted to a position at which the value is smallest. Patent Document 4 discloses a focal adjustment method using a neural network. In this method, the neural network learns feature parameters (density covariance, density contrast, density derivative, etc.) of standard particle images at multiple focal positions in advance. The learned results are loaded in the device, and the focal adjustment is performed on the basis thereof. Patent Document 5 discloses a method using a covariance value in an R image of the standard particle, instead of the area used in Patent Document 3. This is based on a nature that the standard particle at the in-focus position appears in the middle between a white, shining state and a dark state. In the disclosed method, the position of the flow cell or the field lens is adjusted to a position at which the density covariance (covariance) is equal to a substantially center value between the largest and smallest values.

A method of checking the in-focus position and the thickness of the flow of the sample liquid regarding (2) is described in Patent Document 5, for example. Patent Document 5 discloses a method in which the displacement from the in-focus point and the thickness of the flow of the sample liquid are checked by using distribution of the aforementioned covariance values in a relationship diagram between the covariance values and sample widths (the horizontal direction of the static images). It is judged as out of focus when the covariance values are different from the value at the in-focus position. The flow of the sample liquid is judged as thicker when the dispersion of the covariance values (the distribution of the covariance values) is large.

PRIOR ART DOCUMENTS

Patent Documents

Patent Document 1: JP 5-296915
Patent Document 2: JP 63-94156
Patent Document 3: JP 2007-304059
Patent Document 4: JP 9-311102
Patent Document 5: JP 2002-62251

SUMMARY OF THE INVENTION

Problems to be Solved by the Invention

For the in-focus point adjustment for particle images regarding (1) mentioned above, the method of Patent Document 3 uses area values as the parameters for the focal adjustment. As we checked through experiments, we found that as shown in FIG. 1, when the particle size of each standard particle used for the focal adjustment is as small as 1 the area thereof at the in-focus position appear smallest, but as the particle size becomes larger, the position indicating the smallest area value becomes displaced farther from the in-focus position.

The method of Patent Document 4 uses a neural network for the focal adjustment. Using a neural network requires learning with feature parameters obtained from standard particle images at various positions in advance. Moreover, the learning needs to be done with feature parameters obtained from standard particle images concerning day-to-day differences and device-to-device differences, thereby requiring a long time for data collection. In addition, it takes time for the neural network to learn as well.

The method of Patent Document 5 uses a covariance value as the parameter for the focal adjustment. The relationship between the covariance values and the focal positions is as shown in FIG. 2 and is not a monotonic decrease. Thus, it is difficult to determine in which direction to move the flow cell or the field lens in a case of a state of, for example, the arrow A in the diagram at the start of the focal adjustment.

For the method of checking the in-focus position and the thickness of the flow of the sample liquid regarding (2) mentioned above, the method of Patent Document 5 uses covariance values. As shown in FIG. 3, in a case of using this method to judge the thickness of the flow of the sample liquid, covariance values spread in a range of Δ1 when the sample thickness is d1, for example. However, when the flow is shifted to a position of d2 having the same width as d1 as a result of displacement of the in-focus position, dispersion in the distribution is Δ2, which is different from Δ1. For this reason, it is difficult to accurately know the thickness of the flow by using covariance values.

In view of the above, an object of the present invention is to provide a method and device for accurately and efficiently adjusting an in-focus position and then also for accurately checking displacement of the in-focus position and the thickness of the flow of a sample liquid.

Means for Solving the Problems

To solve the above problems, a flow type particle image analysis method of the present invention comprises the steps of: causing a sample liquid containing spherical standard particles to flow through a flow cell, and acquiring a static image of the standard particles by capturing an image of the standard particles by means of an imaging unit including a field lens, the standard particles being made of a same substance; calculating, from the static image, any one of a ratio between a density value around a center of a particle image and a density value around an outline thereof, a difference between the density value around the center of the particle image and the density value around the outline thereof, and a density value around the center of the particle image, the any one of the ratio, the difference, and the density value being calculated as a particle image feature parameter value; and performing focal adjustment of the imaging unit on the basis of the parameter value. This configuration makes it possible to perform focal adjustment using standard particles of various particle sizes and also to figure out the state at the startup of the device (at the start of the focal adjustment). Accordingly, the focal adjustment can be performed efficiently.

Moreover, the flow type particle image analysis method of the present invention comprises the steps of causing the sample liquid containing spherical standard particles to flow through the flow cell, and acquiring static images of the standard particles by capturing images of the standard particles by means of an imaging unit, the standard particles being made of a same substance; extracting, from the static images, particle image feature parameter values indicating focal positions of the imaging unit; converting the parameter values into focal positions; and obtaining information on a thickness of the sample liquid on the basis of dispersion of the converted focal positions. As each of the particle image feature parameter values, any one of a ratio between a density value around a center of a corresponding particle image and a density value around an outline thereof, a difference between the density value around the center of the particle image and the density value around the outline thereof, and a density value around the center of the particle image may be used. This configuration makes it possible to check the displacement of the in-focus position and the thickness of the flow of the sample liquid on the basis of the values of the focal positions and dispersion thereof.

Furthermore, a flow type particle image analysis device of the present invention comprises: a flow cell through which a sample liquid is caused to flow with a sheath liquid surrounding the sample liquid; a pulsed light source for illuminating the flow cell; an imaging unit including a field lens; a drive device for changing a distance between the flow cell and the field lens; a device for causing the sample liquid containing spherical standard particles to flow through the flow cell, and acquiring a static image of the standard particles by capturing an image of the standard particles by means of the imaging unit, the standard particles being made of a same substance; a device for calculating, from the static image, any one of a ratio between a density value around a center of a particle image and a density value around an outline thereof, a difference between the density value around the center of the particle image and the density value around the outline thereof, and a density value around the center of the particle image, the any one of the ratio, the difference, and the density value being calculated as a particle image feature parameter value; and a device for performing focal adjustment of the imaging unit by changing the distance between the flow cell and the field lens by means of the drive device on the basis of the parameter value. Alternatively, the flow type particle image analysis device comprises: a device for converting the parameter value into a focal position of the imaging unit; and a device for obtaining information on an in-focus position on the basis of the focal position. Alternatively, the flow type particle image analysis device may comprise: a device for converting the parameter values into focal positions; and a device for obtaining information on a thickness of the sample liquid on the basis of dispersion of the focal positions.

Effects of the Invention

According to the in-focus point adjustment method of the present invention, it is possible to accurately and efficiently perform in-focus point adjustment using standard particles of various particle sizes. Moreover, according to the checking method using the parameters of the present invention, it is possible to accurately check the in-focus position and the thickness of the flow of the sample liquid.

MODES FOR CARRYING OUT THE INVENTION

Hereinafter, embodiments of the present invention will be described.

Embodiment 1

An embodiment of the present invention will be described below by using the drawings.

Figure 1:
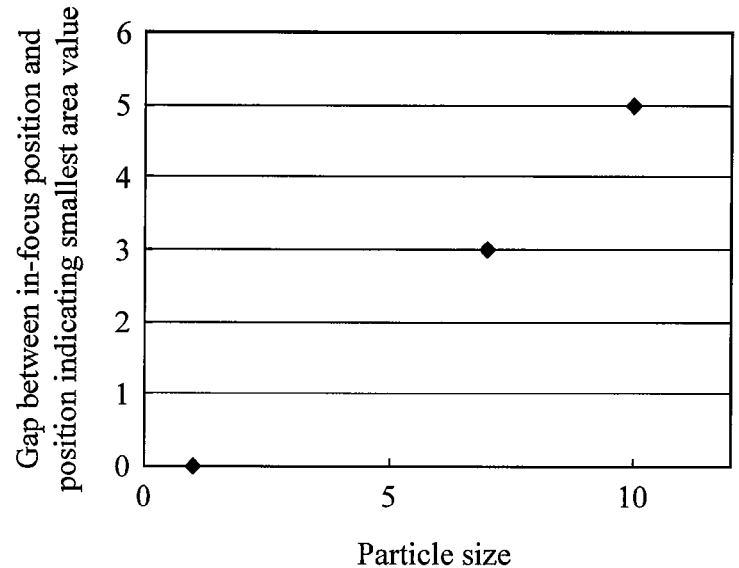
FIG. 1 is a distribution diagram of particle sizes and gaps between an in-focus position and positions indicating smallest area values for the particle sizes.
Figure 2:
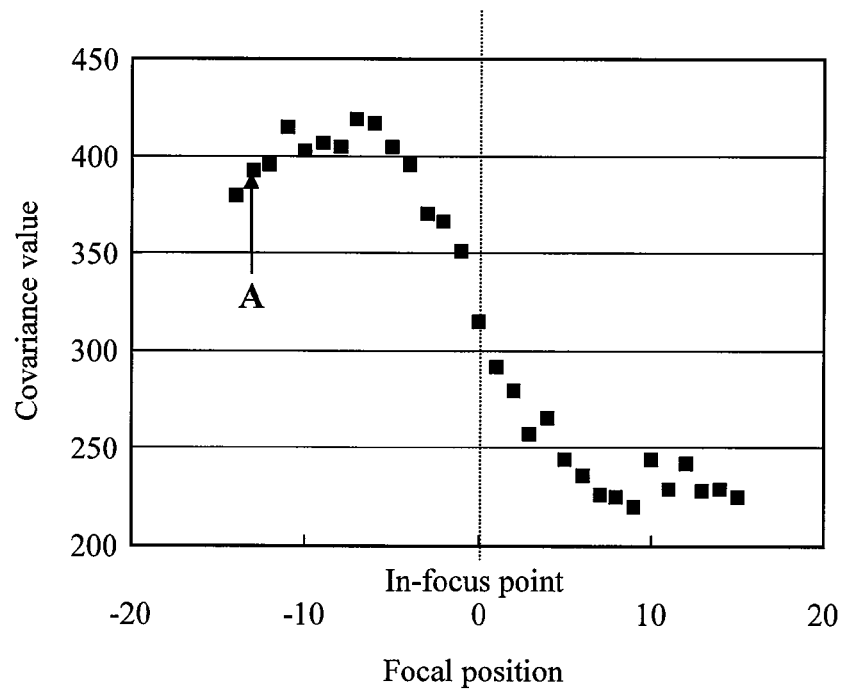
FIG. 2 is a diagram showing an example of the relationship between covariance values and focal positions.
Figure 3:
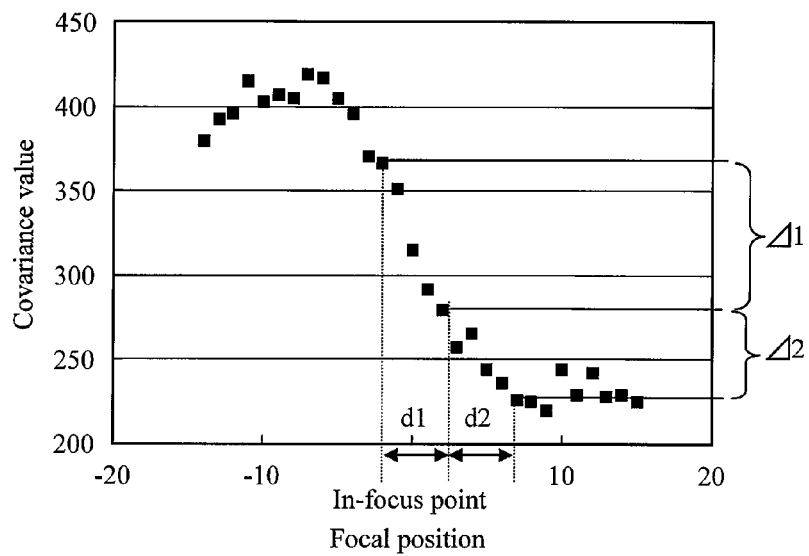
FIG. 3 is a diagram showing an example of the distribution of covariance values and focal positions.
Figure 4:
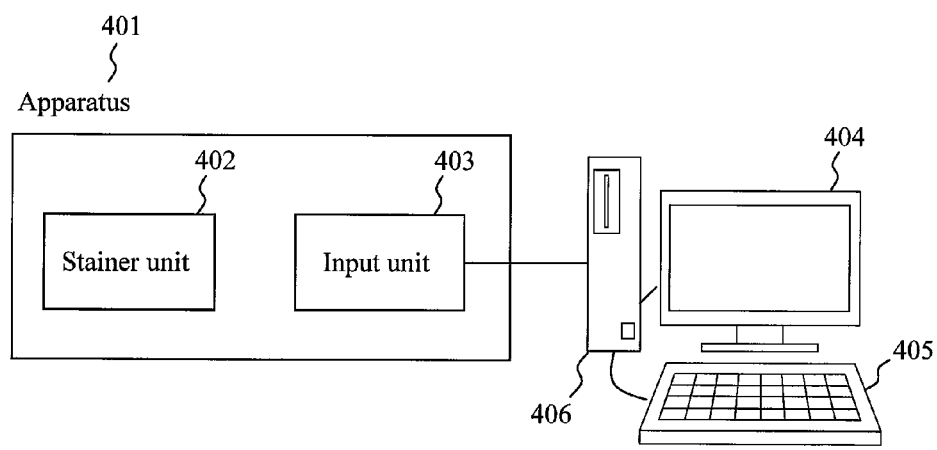
FIG. 4 is a diagram for describing an example of the configuration of the flow type particle image analysis device.

FIG. 4 is a diagram for describing an example of the configuration of a flow type particle image analysis device to which the present invention is applied. In an apparatus 401, a stainer unit 402 adds a stain to a sample, and after the elapse of a given period of time, an input unit 403 captures magnified static images of particles in the sample. The captured images are transferred to an image processing device 406, in which the particles in the samples are classified through image pattern recognition to count the types of particles contained in the sample of a single subject and also the frequency of appearance thereof. As the image processing device 406, a general-purpose personal computer including a display 404 and a keyboard 405 is used, for example. The counted results are reported to the operator through the display 404. A memory inside the image processing device 406 stores data such as images captured by the input unit 403, measurement results and classification results of object regions obtained by the image processing device 406, as well as image feature parameters obtained in the middle of the image pattern recognition. Moreover, the image processing device 406 additionally has a review function. The review function allows the operator to display any image and execute correction in automatic classification as well as visual subclassification.

Figure 5:
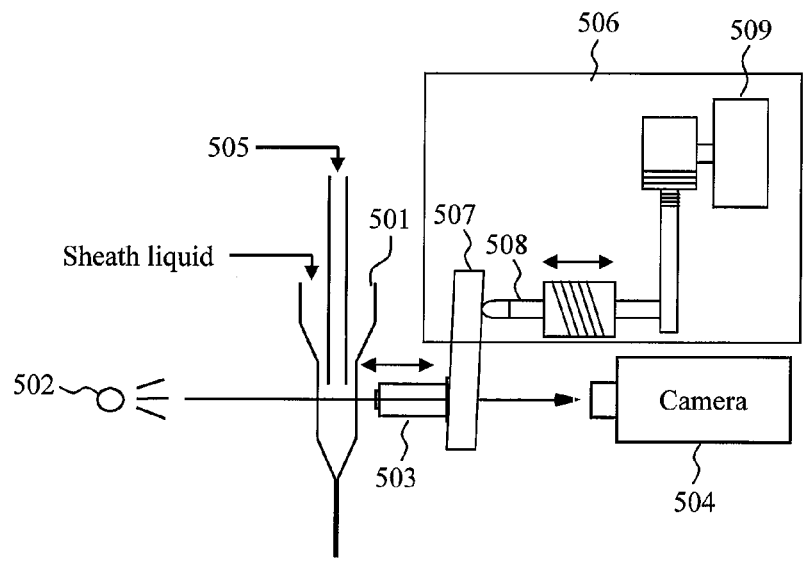
FIG. 5 is a diagram for describing an example of the configuration of an input unit of the flow type particle image analysis device.

FIG. 5 is a configuration diagram of the input unit 403 constituting the apparatus 401. The input unit 403 uses a flow cell 501 to create a wide, thin and flat flow of a sample 505 between a field lens 503 and a pulsed lamp 502. The sample 505 is surrounded by a sheath flow on an outer side thereof and is caused to flow to traverse an optical axis. The flow of the sample 505 formed by the flow cell 501 is irradiated instantaneously with light from the pulsed lamp 502, and a camera 504 captures, as a static image, an image of a particle in the sample 505 magnified by the field lens 503. As the camera 504, a CCD color camera, a CMOS color camera, or the like can be used, for example. The image thus obtained is transferred to the image processing device 406.

The field lens 503 can be moved by a focusing mechanism 506. Rotation of a motor 509 in the focusing mechanism 506 gradually moves a feed screw 508, which in turn moves the field lens 503 engaged with an arm 507 in the front-rear direction along the optical axis. By adjusting the distance (focal position) between the flow cell 501 and the field lens 503, in-focus point adjustment can be achieved. Note that the object to be moved by the focusing mechanism 506 is not limited to the field lens 503, and may be the flow cell 501 instead.

In the in-focus point adjustment, a sample liquid which contains many standard particles made of the same material and having spherical shapes with the same size is used as the sample 505. As the standard particles, commercial transparent spherical particles made of polyethylene or polystyrene are used, for example. The field lens 503 is moved by using the focusing mechanism 506 to change the focal position of the imaging system, and multiple static images of standard particles are captured at multiple different focal positions that are set within the flow in the flow cell. The images thus obtained are transferred to the image processing device 406.

Figure 6:
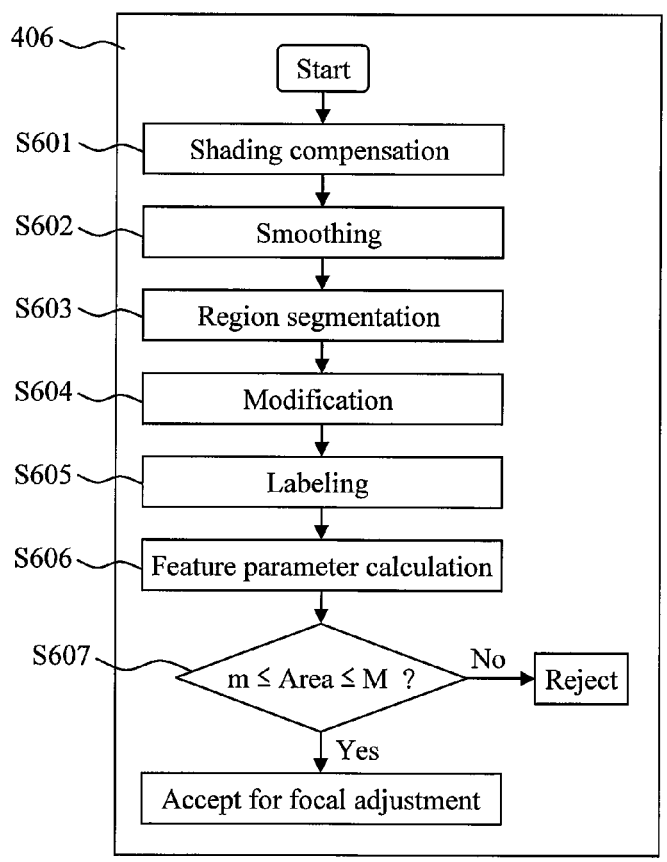
FIG. 6 is a diagram for describing a method of image processing performed during in-focus point adjustment of the flow type particle image analysis device.

FIG. 6 is a diagram for describing details of a method of image processing performed by the image processing device 406 during in-focus point adjustment.

An image of a standard particle captured by the camera 504 is transferred to the image processing device 406 as digital data.

In shading compensation step S601, density unevenness in the image attributable to the characteristics of the optical system is removed.

In smoothing step S602, noise removal is performed. As a means for this, a known technique such as moving average or median filter can be used, for example. The smoothing may be not performed.

In region segmentation step S603, the image capturing the standard particle is segmented into a background region and object regions, and a binary image is created in which the background region has a value of 0 and the object regions have a value of 1.

In modification step S604, correction and reshaping are performed on the binary image, such as hole filling on the object regions and noise removal on the background region. For means for these, known techniques including filtering such as dilation and erosion can be used, for example.

In labeling step S605, labeling is performed for each connected component in the binary image to number them so that multiple objects in the image can be uniquely identified.

In feature parameter calculation step S606, feature parameters such as area and later-described focal adjustment parameter are calculated for each numbered object region.

In step S607, it is judged whether or not the obtained object region is a single standard particle. If m<(area of object region)<M is satisfied, the object region is judged as a single standard particle, accepting the image as a focal adjustment image, and then the process proceeds to the next step. If m<(area of object region)<M is not satisfied, the object region is judged as an image of multiple, connected standard particles or of a component other than the standard particle, and is rejected. Here, optimum values are figured out experimentally in advance for m and M.

Note that all or part of the processes shown in FIG. 6 can be done by hardware.

Figure 7:
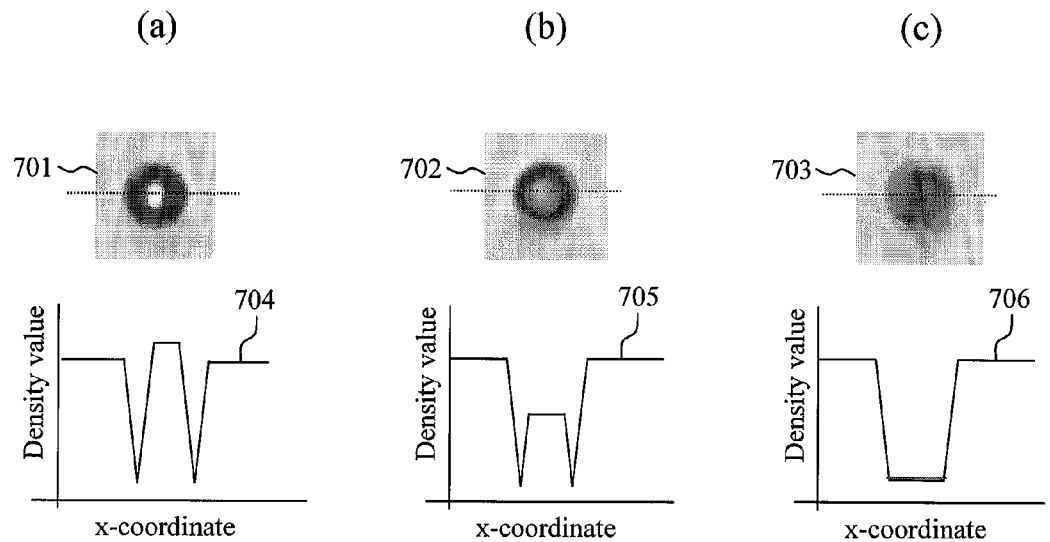
FIG. 7 is a diagram for describing example images of a standard particle at representative focal positions and example schematic charts of density profiles in the x direction passing through the center of the standard particle.

FIG. 7 shows example images of a standard particle at representative focal positions and schematic diagrams of density profiles in the x-direction passing through the center of the standard particle. Part (a) of FIG. 7 shows a case where the focal position of the imaging system including the field lens 503 and camera 504 in FIG. 5 is located on a far side of the standard particle. Part (b) of FIG. 7 shows a case where the focal position of the imaging system coincides with the standard particle, and the standard particle is in focus. Part (c) of FIG. 7 shows a case where the focal position of the imaging system is located on a near side of the standard particle.

As shown in Part (a) of FIG. 7, a standard particle image 701 of the case where the focal position of the imaging system is on the far side of the standard particle is such that a center portion of the standard particle is brighter than the background region thereof. A density profile 704 of this case shows the highest density value around the center of the particle, the lowest density value at each outline portion of the particle, and, in the background portion, a density value higher than the outline portion but lower than the center portion. In contrast, as shown in Part (c) of FIG. 7, a standard particle image 703 of the case where the focal position of the imaging system is on the near side of the standard particle has no distinct feature in the center portion. As illustrated, a density profile 706 of this case shows a low density value in the whole particle portion, thereby showing no change between the density value around the center portion of the particle and the density value at the outline portion. On the other hand, as shown in Part (b) of FIG. 7, a standard particle image 702 at the in-focus position is such that the center portion of the particle has a brightness between that of the bright background and that of the dark outline portion. A density profile 705 of this case shows characteristic density values in the center portion. In sum, the density profile 705 passing through the center of the standard particle shows a moderate density value in the center portion of the particle, a lower density value in the outline portion of the particle, and a higher density value in the background region than the density value of the center portion of the particle.

Figure 8:
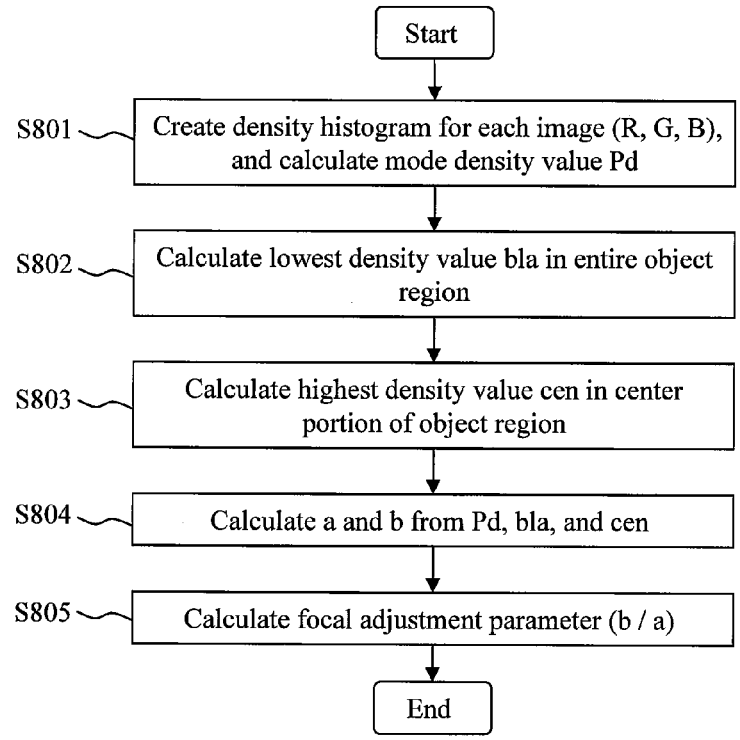
FIG. 8 is a diagram for describing a detailed procedure to figure out a focal adjustment parameter (center density ratio).

FIG. 8 is a diagram showing a detailed procedure to figure out the focal adjustment parameter (center density ratio) to be calculated in the feature parameter calculation step S606. In addition, FIG. 9 is a diagram showing a typical density profile obtained from the image of the standard particle, the density profile passing through the center of the standard particle.

Figure 9:
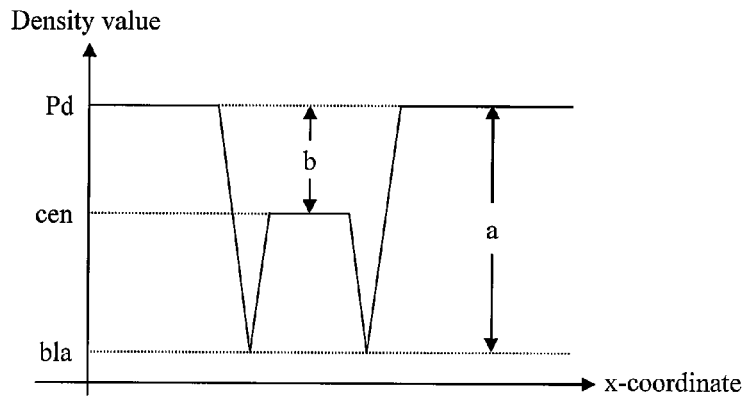
FIG. 9 is a diagram for describing a focal adjustment parameter.

In step S801 in FIG. 8, a density value Pd shown in FIG. 9 is figured out. The density value Pd corresponds to a background level in each image. The background level can be figured out by finding a mode density value in a density histogram created for each image.

In step S802, a density value bla shown in FIG. 9 is figured out. The density value bla is a density value around the outline of the object region representing the standard particle and shows the lowest (darkest) value among the density values in the object region. The density value bla is figured out as the lowest density value in the entire object region.

In step S803, a density value cen shown in FIG. 9 is figured out. The density value cen is a density value around the center of the object region and shows the highest (brightest) value among the density values in the center portion of the object region. The density value cen is figured out as the highest density value in one or more pixels including the center pixel of the object region. Note that as for the number of pixels in the center portion, an optimum number of pixels is figured out experimentally in advance on the basis of the particle size of the standard particle to be used. Moreover, the density value cen is not limited to the highest density value, and the average density value of one or more pixels including the center pixel may be used instead.

In step S804, the density values Pd, cen, and bla are used to figured out a value a (the difference between the background level in each image and the density value around the outline of the object region) and a value b (the difference between the background level in each image and the density value around the center of the object region) shown in FIG. 9. Specifically, the values are calculated from the following equations (1) and (2), respectively.

$$a = Pd - bla \quad (1)$$

$$b = Pd - cen \quad (2)$$

In step S805, a focal adjustment parameter (center density ratio) is calculated from the following equation (3) by using the values a and b.

$$\text{Focal adjustment parameter} = b/a \quad (3)$$

A value other than the above center density ratio may be used as the focal adjustment parameter. The following will describe a center density difference and a center density value as examples of the focal adjustment parameter other than the center density ratio.

Figure 10:
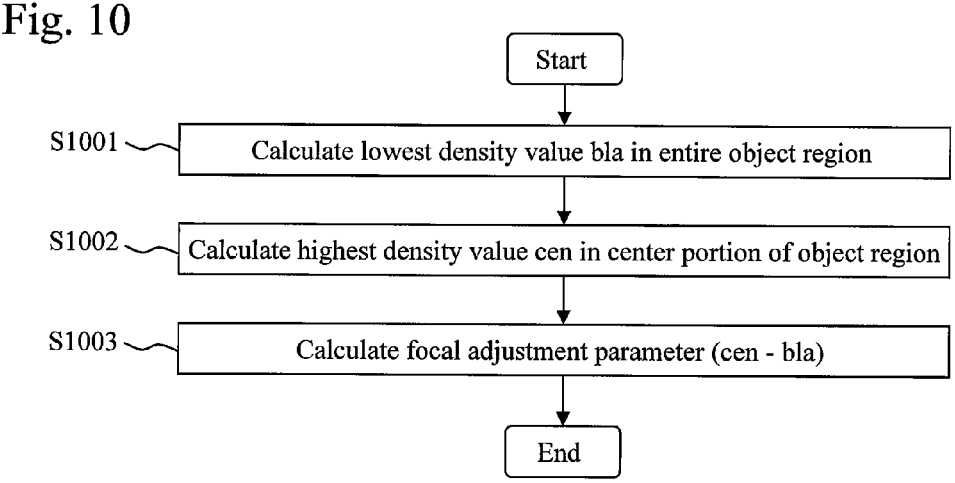
FIG. 10 is a diagram for describing a detailed procedure to figure out a focal adjustment parameter (center density difference).

FIG. 10 is a diagram showing a detailed procedure employed in a case where a center density difference is used as the focal adjustment parameter to be calculated in the feature parameter calculation step S606.

In step S1001, the density value bla around the outline of the object region is figured out. The method shown in step S802 in FIG. 8 may be used to figure out the density value bla.

In step S1002, the density value cen around the center of the object region is figured out. The method shown in step S803 in FIG. 8 may be used to figure out the density value cen.

In step S1003, the focal adjustment parameter (center density difference) is calculated from the following equation (4) by using the density value bla figured out in step S1001 and the density value cen figured out in step S1002.

$$\text{Focal adjustment parameter} = cen - bla \quad (4)$$

Figure 11:
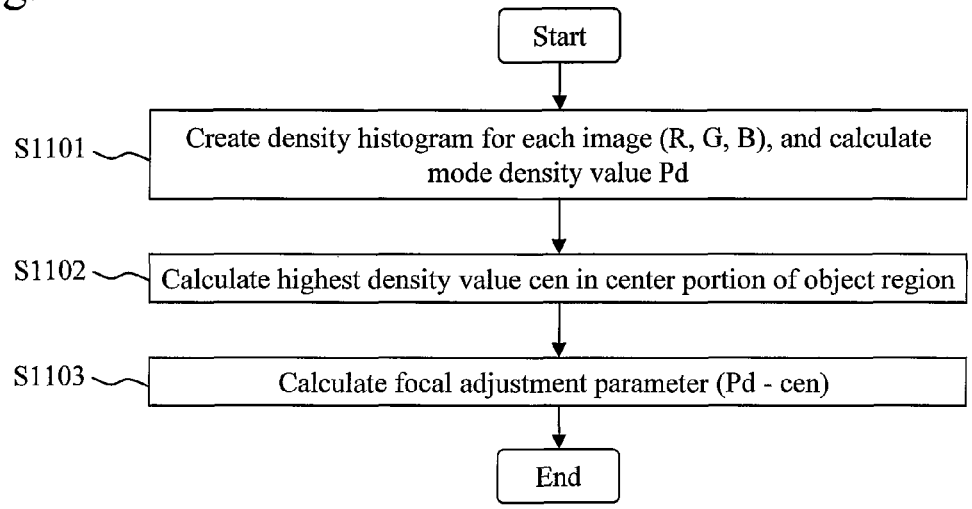
FIG. 11 is a diagram for describing a detailed procedure to figure out a focal adjustment parameter (center density).

FIG. 11 is a diagram showing a detailed procedure employed in a case where a center density value is used as the focal adjustment parameter to be calculated in the feature parameter calculation step S606.

In step S1101, the background level in each image is figured out. The method shown in step S801 in FIG. 8 may be used to figure out the background level.

In step S1102, the density value cen around the center of the object region is figured out. The method shown in step S803 in FIG. 8 may be used to figure out the density value cen.

In Step S1103, the focal adjustment parameter (center density difference) is calculated from the following equation (5) by using the density value Pd figured out in step S1101 and the density value cen figured out in Step S1102.

$$\text{Focal adjustment parameter} = PD - cen \quad (5)$$

Note that the center density value is not limited to (Pd−cen), and the value of cen itself may be used instead.

Moreover, as for which one of the center density ratio, the center density difference, and the center density value should be used as the focal adjustment parameter, a parameter that is optimum for the focal adjustment may be selected on the basis of the characteristics of the optical system incorporated in the device.

Figure 12:
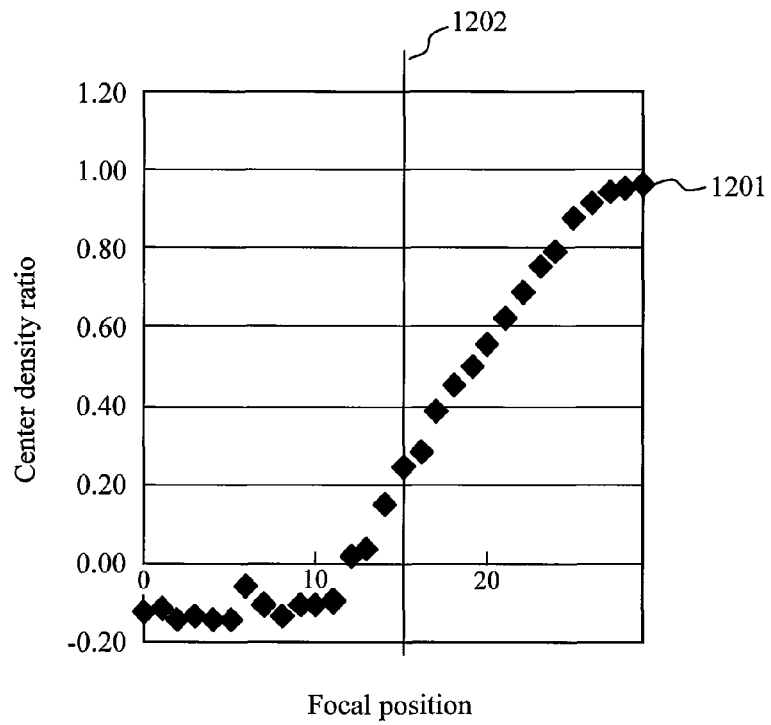
FIG. 12 is a diagram showing an example of the relationship between the focal adjustment parameters and focal positions.

FIG. 12 is a diagram showing example focal adjustment parameter (center density ratio) values calculated from images captured at focal positions that are set within the flow cell by moving the field lens 503 for 30 points on a 1-μm basis in a condition where a standard particle with a particle size of 10 μm is used as the standard particle sample 505 shown in FIG. 5, for example. A symbol 1201 is a plot of the average values of the focal adjustment parameters each calculated from approximately 100 standard particle images obtained at the corresponding focal position. Note that as for the particle size of the standard particle to be used, a size that is optimum for the component which the flow type particle image analysis device is targeting may be selected. Moreover, as for the pitch by which to move the field lens, an optimum pitch may be determined experimentally in advance on the basis of the particle size of the standard particle to be used. In the calculation of the focal adjustment parameters, density values of a color which is most sensitive based on the color characteristics of the standard particle and the spectral characteristics of the camera are selected and used. As for the number of standard particle images to be collected at each focal position, an optimum number may be figured out experimentally in advance on the basis of dispersion of the focal adjustment parameters and the characteristics of the camera.

As shown in FIG. 12, the relationship between the focal position and the focal adjustment parameter exhibits a monotonic increase over a wide range, and an in-focus position 1202 is at a position where the focal adjustment parameter is substantially in the middle between the smallest value and the largest value. For instance, in the case of the example in FIG. 12, a focal adjustment parameter (center density ratio) value at the in-focus position is 0.28. Note that as for the in-focus position, an optimum position may be determined experimentally in advance on the basis of the particle size of the standard particle to be used and the characteristics of the optical system. Although the description is given here for the case of using the center density ratio as the focal adjustment parameter, the value of the focal adjustment parameter at the in-focus position can be determined in a similar manner also in a case of using the center density value or center density value as the focal adjustment parameter.

Figure 13:
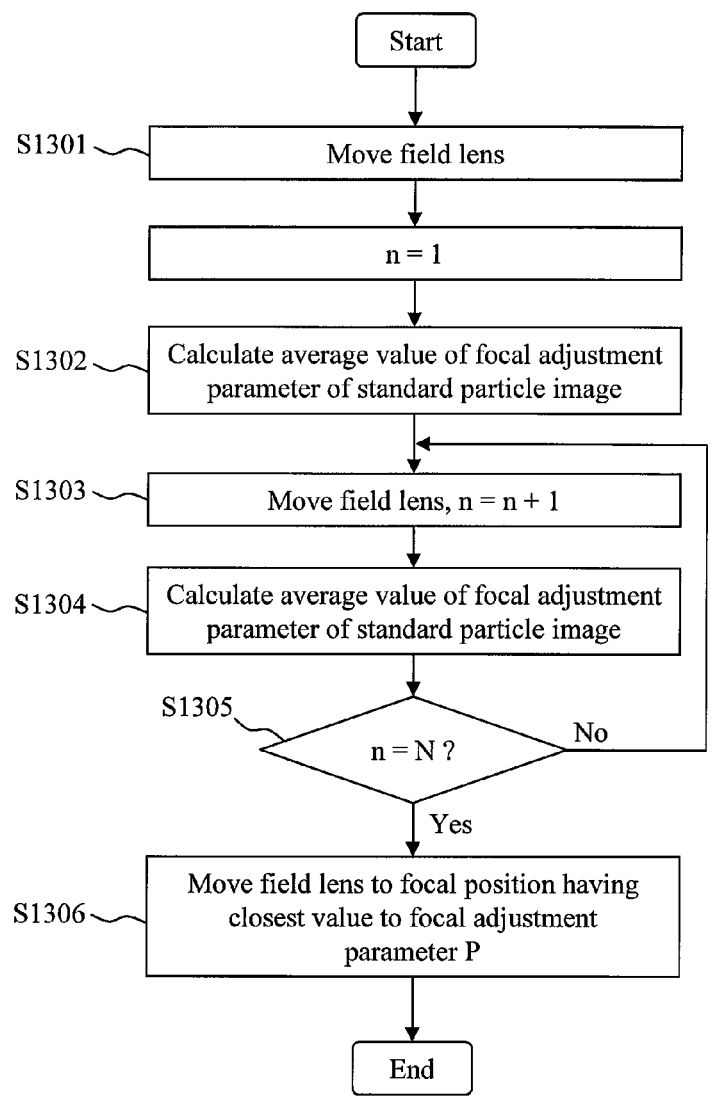
FIG. 13 is a diagram for describing a detailed procedure in an in-focus point adjustment method.

FIG. 13 is a diagram showing an example detailed procedure in the in-focus point adjustment method of the present invention.

In Step S1301, the field lens is moved to a predetermined initial position. This may be done by settings allowing automatic movement at the startup of the device.

In step S1302, the average value of focal adjustment parameters at the initial position is calculated.

In Step S1303, the field lens is moved 1 μm, for example. The moving pitch and moving direction are set experimentally in advance. In addition, a count value n is incremented by 1.

In Step S1304, the average value of focal adjustment parameters at the position after the movement is calculated.

In Step S1305, it is judged whether or not the number (n) of times the field lens is moved has reached a number determined experimentally in advance. If n=N is satisfied, the field lens is judged as having been moved the predetermined number of times, and the process proceeds to Step S1306. If n=N is not satisfied, the process returns to Step S1303 and repeats the movement of the field lens and the calculation of the average value of the focal adjustment parameters at the moved focal position until Step S1305 is satisfied. Note that as for N, an optimum number is figured out in advance on the basis of the particle size of the standard particle and the focal adjustment parameter.

In step S1306, the field lens is moved to the focal position, of all the focal positions obtained, at which the focal adjustment parameters show the closest value to P. P is a value determined experimentally in advance, and is for instance 0.28 in the case of the example in FIG. 12.

Note that in step S1301, the initial position may be the very position at the startup of the device, instead of the predetermined initial position. In this case, in the movement of the field lens in Step S1303, the moving direction of the field lens is determined on the basis of where the focal adjustment parameter value figured out in step S1302 is located in a pre-obtained relationship diagram, which is FIG. 12, for example.

Figure 14:
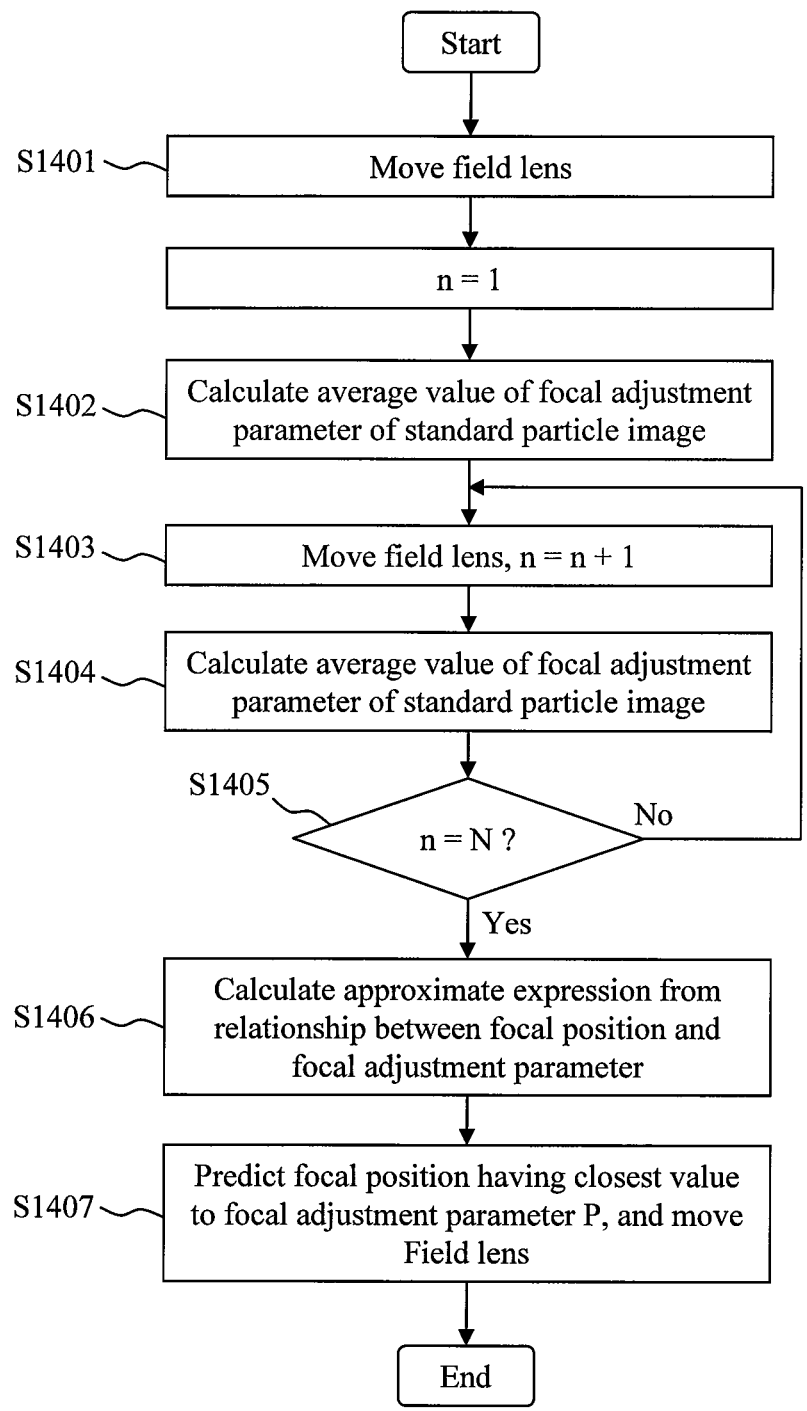
FIG. 14 is a diagram for describing a detailed procedure in a focal adjustment method using an approximate expression.

FIG. 14 is a diagram showing an example detailed procedure in a in-focus point adjustment method using an approximate expression.

In Step S1401, the field lens is moved to a predetermined initial position. This may be done by settings allowing automatic movement at the startup of the device.

In Step S1402, the average value of focal adjustment parameters at the initial position is calculated.

In Step S1403, the field lens is moved 3 μm, for example. The moving pitch and moving direction are set experimentally in advance. In addition, a count value n is incremented by 1.

In step S1404, the average value of focal adjustment parameters at the position after the movement is calculated.

In Step S1405, it is judged whether or not the number (n) of times the field lens is moved has reached a number determined experimentally in advance. If n=N is satisfied, the field lens is judged as having been moved the predetermined number of times, and the process proceeds to Step S1406. If n=N is not satisfied, the process returns to Step S1403 and repeats the movement of the field lens and the calculation of the average value of the focal adjustment parameters at the moved focal position until step S1405 is satisfied. Note that as for N, an optimum number is figured out in advance on the basis of the particle size of the standard particle and the focal adjustment parameter.

In Step S1406, an approximate expression is calculated from the focal positions and the focal adjustment parameter values which have been obtained at the multiple different positions so far up to Step S1405. The approximate expression may be figured out by using a known function such as sigmoid function, for example.

In Step S1407, the approximate expression figured out in Step S1406 is used to predict an in-focus position representing a focal adjustment parameter value P, and the field lens is moved thereto. P is a value determined experimentally in advance, and is for instance 0.28 in the case of the example in FIG. 12.

Note that although the field lens is moved to move the focal position of the imaging system within the flow cell in the examples of FIGS. 13 and 14, the flow cell may be moved to set the focal position of the imaging system to each of the multiple different positions within the flow cell, instead of moving the field lens.

Figure 15:
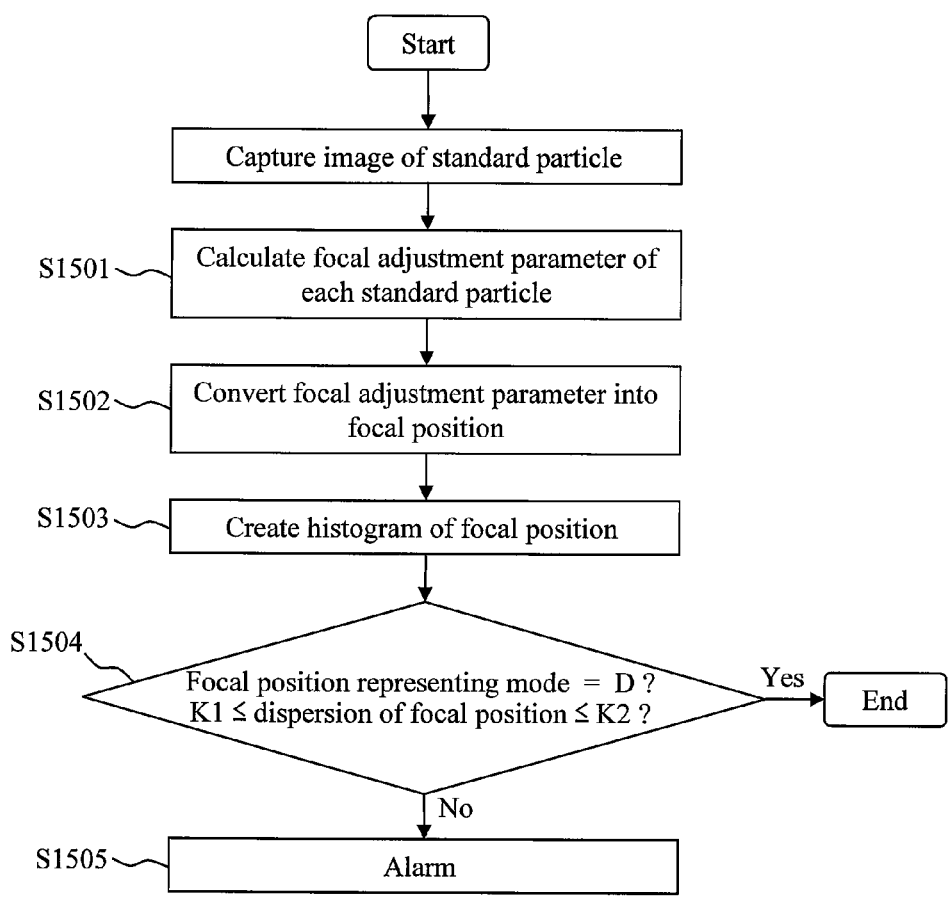
FIG. 15 is a diagram for describing a detailed procedure in a method of checking the displacement of the in-focus position and the thickness of the flow of a sample liquid.

FIG. 15 is a diagram showing a detailed procedure in a method of checking the displacement of the in-focus position and the thickness of the flow of the sample liquid after the focal position of the imaging system is once adjusted to the in-focus position. The shape of the flow of the sample may possibly be thicker than a preset value due to such a reason that a predetermined amount of the sheath liquid surrounding the sample liquid shown in FIG. 5 is not flowing or the flow of the sheath liquid is uneven. It is therefore desirable to regularly check the position of the in-focus point and the thickness of the flow of the sample liquid. The checking interval is determined based on the number of subjects, a given time interval, or the like, for example.

As the procedure, as mentioned above, the standard particles being the sample are caused to flow. Then, in step S1501, the field lens is held unmoved and maintained in its current position, and the focal adjustment parameter of each standard particle is calculated from one or more images. The method of calculating the particle size of the standard particle to be used and the focal adjustment parameter is the same as that for the in-focus point adjustment.

In Step S1502, the focal adjustment parameters are converted into focal positions. For the conversion, the approximate expression figured out in S1406 shown in FIG. 14 is used. Note that an approximate expression figured out experimentally in advance may be used instead.

In step S1503, a histogram of the focal positions thus figured out is created.

In Step S1504, it is judged whether or not the in-focus position is displaced and whether or not the thickness of the flow of the sample liquid is normal. The in-focus position and the thickness of the flow of the sample liquid are judged as normal if the following points are satisfied: the focal position representing the mode in the histogram=D (D is a focal position when the focal position of the imaging system is adjusted to the in-focus position); and K1<dispersion of the focal positions<K2. In this case, the checking is terminated. If these points are not satisfied, an alarm is issued in Step S1505. As the alarm, it is possible to specifically display information indicating that the in-focus point is displaced and the thickness of the flow of the sample liquid is not normal. It is also possible to notify with an alarm.

For the dispersion of the focal positions, it is possible to use for example: (a) the difference (width) between a higher position and a lower position representing the half value of the mode of the histogram; (b) the difference (width) between a higher position and a lower position with respect to the position of the mean±(x×sigma) (x is a predetermined constant such as 1, for example) under the assumption that the histogram is a normal distribution; or the like. Moreover, K1 and K2 may be figured out experimentally in advance by using a histogram of a case where the thickness of the flow of the sample liquid is normal. Alternatively, K1 and K2 may be figured out from a histogram obtained at the in-focus position after the in-focus point adjustment.

Figure 16:
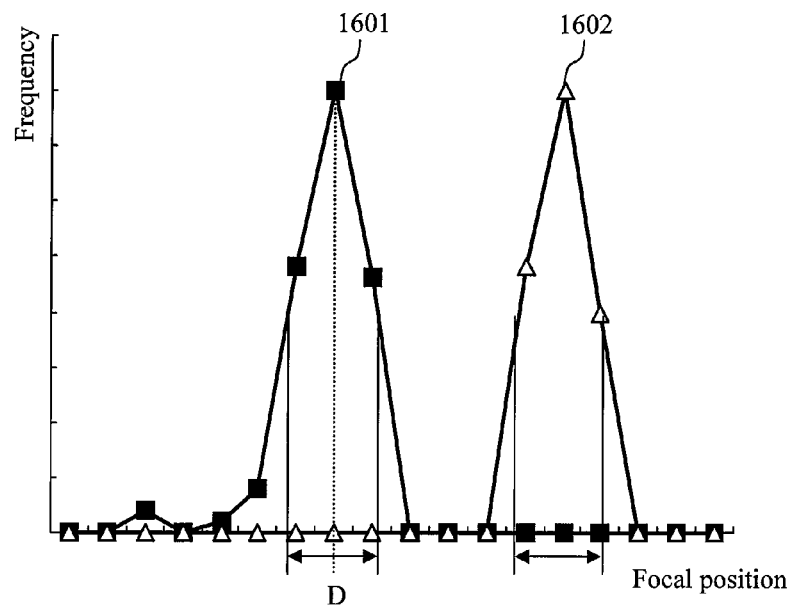
FIG. 16 is a diagram showing an example focal position histogram of a case where the in-focus point is displaced.

FIG. 16 shows an example histogram of a case where the thickness of the flow of the sample liquid is normal but the in-focus position is displaced, for example. A symbol 1601 shows a histogram of a case where the in-focus position and the thickness of the flow of the sample liquid are normal. A symbol 1602 shows a histogram reflecting a given device condition. It can be seen from the diagram that the focal position in the symbol 1602 representing the mode is displaced from D in the symbol 1601. Moreover, since the displacement is occurring in the positive side, the in-focus position can be judged as being displaced to the positive side. As for the thickness of the flow of the sample liquid, the difference between a higher side and a lower side of the focal position representing the half value of the histogram, for example, is substantially equal to that of the normal symbol 1601. Thereby, the thickness of the flow of the sample liquid can be judged as normal.

Figure 17:
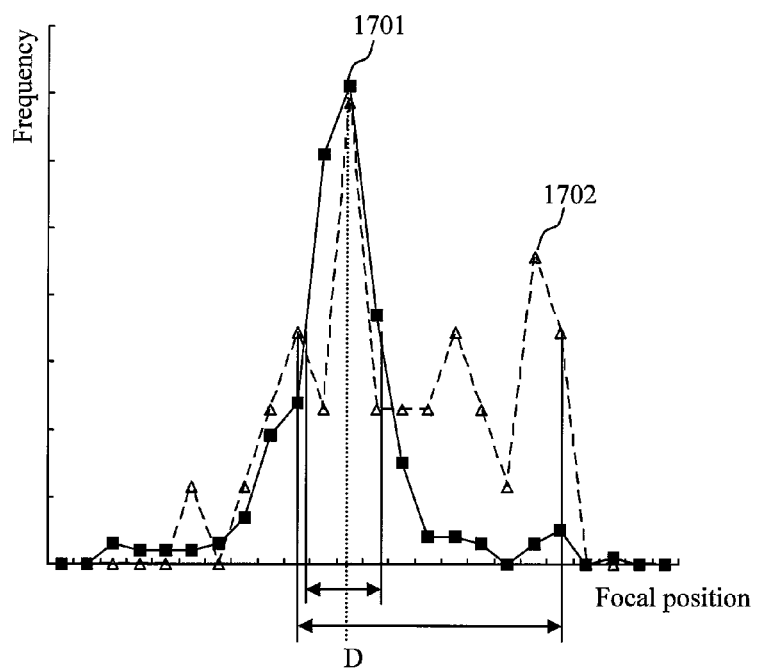
FIG. 17 is a diagram showing an example focal position histogram of a case where the thickness of the flow of the sample liquid is thicker.

FIG. 17 is an example histogram of a case where the in-focus position is normal but the thickness of the flow of the sample liquid is large. A symbol 1701 shows a histogram of a case where the in-focus position and the thickness of the flow of the sample liquid are normal. A symbol 1702 shows a histogram reflecting a given device condition. A focal position in the histogram of the symbol 1702 representing the mode is the same as D in the symbol 1701. Thereby, the in-focus position can be judged as normal. As for the thickness of the flow of the sample liquid, the difference between a higher side and a lower side of the focal position representing the half value of the histogram, for example, is larger in the symbol 1702 than the symbol 1701. Thereby, the thickness of the flow of the sample liquid can be judged as large.

With the in-focus point adjustment method using the focal adjustment parameters of the present invention, it is possible to perform in-focus point adjustment using standard particle of various sizes. Moreover, use of the focal adjustment parameters of the present invention allows a monotonic increase (or decrease) over a wide range in the relationship between the parameter and the focal position, hence making it possible to easily predict the state of the focal point at the startup of the device. Accordingly, the focal adjustment can be done efficiently. Further, figuring out an approximate function from the relationship between the focal position and the focal adjustment parameters makes it possible to easily predict the in-focus position. Accordingly, the focal adjustment can be done efficiently.

Use of the focal adjustment parameters of the present invention allows conversion of parameters into focal positions. Accordingly, the in-focus position of the device can be figured out accurately. Moreover, in a case where the in-focus position is displaced, the direction of the displacement can be figured out accurately. Further, use of the method of checking the thickness of the flow of the sample liquid using the focal adjustment parameters of the present invention allows conversions of parameters into focal positions. Accordingly, the thickness of the flow of the sample liquid can be checked accurately.

Embodiment 2

Figure 18:
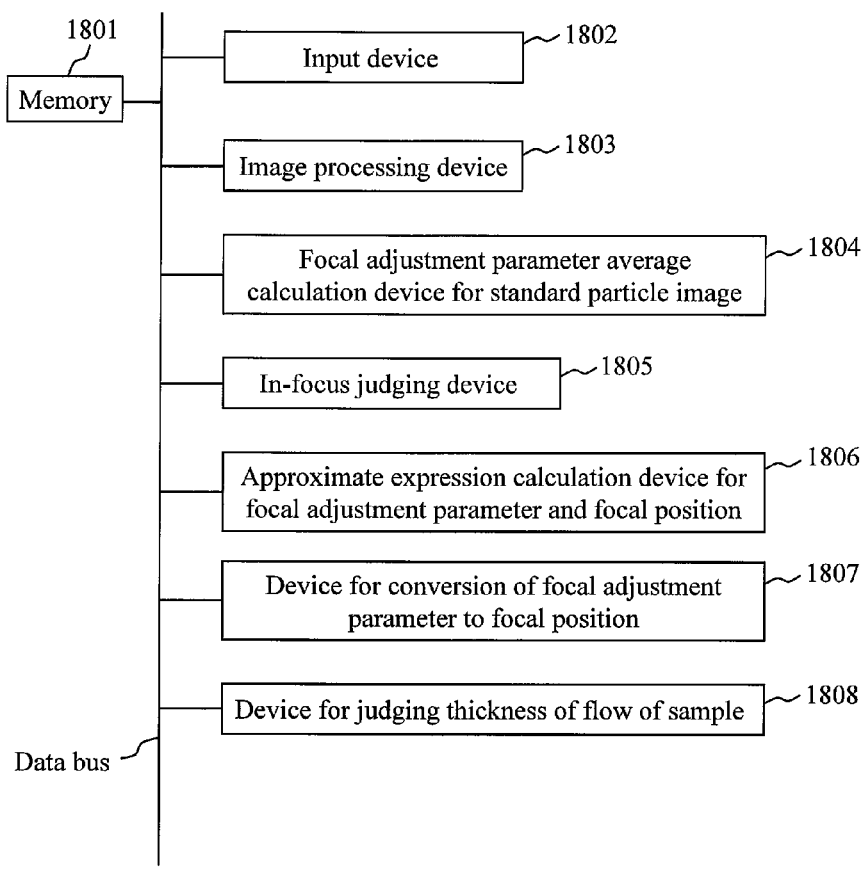
FIG. 18 is a diagram for describing an example of the configuration of the flow type particle image analysis device of the present invention.

FIG. 18 is a diagram for describing an example of the configuration of a device for adjusting the in-focus point of a flow type particle image analysis device of the present invention and for checking the in-focus position and the thickness of the flow of a sample liquid.

In a case of in-focus point adjustment, standard particle images which are captured at multiple focal positions by an input device 1802 such as a camera are transferred to a memory 1801.

The standard particle images are then transferred to an image processing device 1803, in which region segmentation and calculation of feature parameters (area, focal adjustment parameter, etc.) are performed. For the methods of the region segmentation and the feature parameter calculation, the methods described in Embodiment 1 may be used.

Object region images obtained by the region segmentation and the feature parameters are transferred to the memory 1801.

The focal adjustment parameter of each region judged as a single standard particle based on its area, one of the feature parameters, is transferred to a focal adjustment parameter average calculation device 1804 on a focal-position basis, and average values thereof are calculated. The focal adjustment parameter average value calculated at each focal position is transferred to the memory 1801. As the focal adjustment parameter, the center density ratio, center density difference, or center density value described in Embodiment 1, or the like may be used.

The focal adjustment parameter average value calculated at each focal position is then transferred to an in-focus judging device 1805, in which it is judged which one of the focal positions is the in-focus point. For the method of the judgment, the method described in Embodiment 1 may be used. The position judged as the in-focus point is transferred to the memory 1801.

The focal adjustment parameter average value calculated at each focal position is transferred to an approximate expression calculation device 1806, in which an approximate expression of the relationship between the focal adjustment parameter and the focal position is calculated. The calculated approximate expression is transferred to the memory 1801. For the method of figuring out the approximate expression, the method described in Embodiment 1 may be used.

In a case of checking the displacement of the in-focus position and the thickness of the flow of the sample liquid in a state where the in-focus point adjustment has been complete, standard particle images captured by the input device 1802 such as a camera are transferred to the memory 1801.

The standard particle images are then transferred to an image processing device 1803, in which region segmentation and calculation of feature parameters (area, focal adjustment parameter, etc.) are performed. For the methods of the region segmentation and the feature parameter calculation, the methods described in Embodiment 1 may be used. Object region images obtained by the region segmentation and the feature parameters are transferred to the memory 1801.

The focal adjustment parameter of each region judged as a single standard particle based on its area, one of the feature parameters, is transferred to a device 1807 for conversion to focal positions. For the method of the conversion, the method described in Embodiment 1 may be used. The converted focal positions are transferred to the memory 1801.

The converted focal positions are then transferred to the in-focus judging device 1805 and a device 1808 for judging the thickness of the flow of the sample liquid. There, it is judged whether or not the in-focus position is normal and whether or not the thickness of the flow of the sample liquid is normal. For the methods of the judgment, the methods described in Embodiment 1 may be used. The judgment results are transferred to the memory 1801.

With the device configuration of the present invention, it is possible to accurately and efficiently perform in-focus point adjustment using standard particles of various particle sizes. Moreover, it is possible to accurately check the displacement of the in-focus point and the thickness of the flow of the sample liquid.

EXPLANATION OF REFERENCE NUMERALS

401 apparatus
402 stainer unit
403 input unit
404 display
405 keyboard
406 image processing device
501 flow cell
502 pulsed lamp
503 field lens
504 camera
505 sample
506 focusing mechanism
507 arm
508 feed screw
509 motor

The invention claimed is:

1. A flow type particle image analysis method of analyzing a particle image obtained by capturing an image of a sample liquid caused to flow with a sheath liquid surrounding the sample liquid, the method comprising the steps of:
   causing the sample liquid containing spherical standard particles to flow through a flow cell, and acquiring a static image of the standard particles by capturing an image of the standard particles with an imaging unit including a field lens, the standard particles being made of a same substance;
   calculating, from the static image, any one of a ratio between a density value around a center of a particle image and a density value around an outline thereof, and a difference between the density value around the center of the particle image and the density value around the outline thereof, the any one of the ratio and the difference being calculated as a particle image feature parameter value; and
   performing focal adjustment of the imaging unit on the basis of the parameter value.

2. The flow type particle image analysis method according to claim 1, wherein
   the method further comprises the steps of:
     acquiring a plurality of static images at each of a plurality of mutually different focal positions which are set within the flow cell by moving any one of the field lens and the flow cell; and
     calculating an average parameter value for each of the plurality of mutually different focal positions from the static images acquired at the focal position,
   wherein the focal adjustment is performed on the basis of the average parameter values.

3. The flow type particle image analysis method according to claim 2, wherein
   a relationship between the plurality of focal positions and the average parameter values is approximated by a function, and
   the focal adjustment is performed by using the function.

4. A flow type particle image analysis method of analyzing a particle image obtained by capturing an image of a sample liquid caused to flow with a sheath liquid surrounding the sample liquid, the method comprising the steps of:
   causing the sample liquid containing spherical standard particles to flow through a flow cell, and acquiring static images of the standard particles by capturing images of the standard particles with an imaging unit, the standard particles being made of a same substance;
   calculating, from each of the static images, any one of a ratio between a density value around a center of a particle image and a density value around an outline thereof, and a difference between the density value around the center of the particle image and the density value around the outline thereof, the any one of the ratio and the difference being calculated as a particle image feature parameter value;
   converting the parameter values into focal positions of the imaging unit; and
   obtaining information on an in-focus position on the basis of the focal positions.

5. The flow type particle image analysis method according to claim 4, wherein the focal position information is obtained on the basis of a function which approximates a relationship between the focal positions and the parameter values.

6. A flow type particle image analysis method of analyzing a particle image obtained by capturing an image of a sample liquid caused to flow with a sheath liquid surrounding the sample liquid, the method comprising the steps of:
   causing the sample liquid containing spherical standard particles to flow through a flow cell, and acquiring static images of the standard particles by capturing images of the standard particles with an imaging unit, the standard particles being made of a same substance;
   calculating, from each of the static images, any one of a ratio between a density value around a center of a particle image and a density value around an outline thereof, and a difference between the density value around the center of the particle image and the density value around the outline thereof, the any one of the ratio and the difference being calculated as a particle image feature parameter value indicating a focal position of the imaging unit;
   converting the parameter values into focal positions; and obtaining information on a thickness of the sample liquid on the basis of dispersion of the converted focal positions.

7. The flow type particle image analysis method according to claim 6, wherein
a relationship between the focal positions and the parameter values is approximated by a function, and
the parameter values are converted into the focal positions on the basis of the function.

8. A flow type particle image analysis device comprising:
a flow cell through which a sample liquid is caused to flow with a sheath liquid surrounding the sample liquid;
a pulsed light source which illuminates the flow cell;
an imaging unit including a field lens;
a drive device which changes a distance between the flow cell and the field lens;
a device which causes the sample liquid containing spherical standard particles to flow through the flow cell, and acquires a static image of the standard particles by capturing an image of the standard particles with the imaging unit, the standard particles being made of a same substance;
a device which calculates, from the static image, any one of a ratio between a density value around a center of a particle image and a density value around an outline thereof, and a difference between the density value around the center of the particle image and the density value around the outline thereof, the any one of the ratio and the difference being calculated as a particle image feature parameter value; and
a device which performs focal adjustment of the imaging unit by changing the distance between the flow cell and the field lens by the drive device on the basis of the parameter value.

9. A flow type particle image analysis device comprising:
a flow cell which causes a sample liquid to flow therethrough with a sheath liquid surrounding the sample liquid;
a pulsed light source which illuminates the flow cell;
an imaging unit including a field lens;
a drive device which changes a distance between the flow cell and the field lens;
a device which causes the sample liquid containing spherical standard particles to flow through the flow cell, and acquires a static image of the standard particles by capturing an image of the standard particles with the imaging unit, the standard particles being made of a same substance;
a device which calculates, from the static image, any one of a ratio between a density value around a center of a particle image and a density value around an outline thereof, and a difference between the density value around the center of the particle image and the density value around the outline thereof, the any one of the ratio and the difference being calculated as a particle image feature parameter value;
a device which converts the parameter value into a focal position of the imaging unit; and
a device which obtains information on an in-focus position on the basis of the focal position.

10. A flow type particle image analysis device comprising:
a flow cell which causes a sample liquid to flow therethrough with a sheath liquid surrounding the sample liquid;
a pulsed light source which illuminates the flow cell;
an imaging unit including a field lens;
a drive device which changes a distance between the flow cell and the field lens;
a device which causes the sample liquid containing spherical standard particles to flow through the flow cell, and acquires static images of the standard particles by capturing images of the standard particles with the imaging unit, the standard particles being made of a same substance;
a device which calculates, from the static image, any one of a ratio between a density value around a center of a particle image and a density value around an outline thereof, and a difference between the density value around the center of the particle image and the density value around the outline thereof, the any one of the ratio and the difference being calculated as a particle image feature parameter value indicating a focal position of the imaging unit;
a device which converts the parameter values into focal positions; and
a device which obtains information on a thickness of the sample liquid on the basis of dispersion of the focal positions.

* * * * *